(12) United States Patent
Nelson

(10) Patent No.: US 9,498,248 B2
(45) Date of Patent: Nov. 22, 2016

(54) RETAINER FOR IMMOBILIZING AN IMPLANTED CATHETER DURING STYLET RETRACTION, AND STYLET HOLDER FOR USE WITH SAME

(75) Inventor: Brian D. Nelson, Birchwood, MN (US)

(73) Assignee: Medtronic, Inc., Minneapolis, MN (US)

(*) Notice: Subject to any disclaimer, the term of this patent is extended or adjusted under 35 U.S.C. 154(b) by 873 days.

(21) Appl. No.: 13/247,203

(22) Filed: Sep. 28, 2011

(65) Prior Publication Data

US 2012/0083739 A1     Apr. 5, 2012

Related U.S. Application Data

(60) Provisional application No. 61/389,910, filed on Oct. 5, 2010.

(51) Int. Cl.
*A61B 17/34* (2006.01)
*A61M 25/06* (2006.01)

(52) U.S. Cl.
CPC .......... *A61B 17/3403* (2013.01); *A61B 90/11* (2016.02); *A61B 17/3415* (2013.01); *A61B 2017/3407* (2013.01); *A61B 2017/347* (2013.01); *A61M 25/0662* (2013.01); *A61M 2210/0687* (2013.01); *A61M 2210/0693* (2013.01)

(58) Field of Classification Search
CPC .......... A61B 17/3403; A61B 17/3415; A61B 2017/3407; A61B 2017/347; A61B 90/11; A61M 2210/0687; A61M 2210/0693; A61M 25/0662

USPC ........... 604/164.01, 164.04, 164.07, 165.01, 604/165.02, 166.01, 174; 600/408, 429, 600/114; 606/108

See application file for complete search history.

(56) References Cited

U.S. PATENT DOCUMENTS

| 3,822,697 | A | * | 7/1974 | Komiya ........................ 600/114 |
| 3,853,127 | A | | 12/1974 | Spademan |
| 4,311,137 | A | | 1/1982 | Gerard |
| 5,030,205 | A | | 7/1991 | Holdaway et al. |
| 5,126,090 | A | | 6/1992 | Egolf et al. |

(Continued)

FOREIGN PATENT DOCUMENTS

WO   WO 2009/061825 A1   5/2009

OTHER PUBLICATIONS

"CRW Precision Arc Stereotactic System" datasheet. Integra NeuroSciences, Integra LifeSciences Corporation, Plainsboro, NJ, 2009; 12 pages.

(Continued)

*Primary Examiner* — Quynh-Nhu H Vu
(74) *Attorney, Agent, or Firm* — Mueting, Raasch & Gebhardt, P.A.

(57) ABSTRACT

Devices, systems, and methods for immobilizing an implanted catheter tip while a catheter stylet is withdrawn from the catheter. In one embodiment, a cannula system is included that incorporates a catheter retainer securable to an immobilized guide cannula. The retainer may include one or more surfaces that operatively engage the catheter and effectively restrain the catheter relative to a head of the guide cannula. Other embodiments may also include a stylet holder operable to engage the stylet with a consistent and repeatable clamping force that is independent of clinician-applied force.

12 Claims, 10 Drawing Sheets

(56) References Cited

U.S. PATENT DOCUMENTS

| | | | |
|---|---|---|---|
| 5,183,465 | A | 2/1993 | Xanthakos et al. |
| 5,603,703 | A | 2/1997 | Elsberry et al. |
| 6,591,472 | B1 | 7/2003 | Noone et al. |
| 7,730,628 | B2 * | 6/2010 | Hoffman ............... 33/512 |
| 7,879,045 | B2 | 2/2011 | Gielen et al. |
| 2005/0256455 | A1 | 11/2005 | Weststrate et al. |
| 2006/0122628 | A1 | 6/2006 | Solar et al. |
| 2007/0066977 | A1 | 3/2007 | Assell et al. |
| 2008/0161719 | A1 | 7/2008 | Miller et al. |
| 2008/0275466 | A1 * | 11/2008 | Skakoon ............... 606/130 |
| 2009/0143764 | A1 | 6/2009 | Nelson |
| 2009/0187149 | A1 | 7/2009 | Nelson |
| 2010/0030184 | A1 | 2/2010 | Boulis et al. |
| 2011/0009879 | A1 | 1/2011 | Derrick et al. |
| 2011/0040304 | A1 | 2/2011 | Li et al. |

OTHER PUBLICATIONS

U.S. Appl. No. 61/389,910, filed Oct. 5, 2010, Nelson.
U.S. Appl. No. 13/247,149, filed Sep. 28, 2011, Nelson.
"Leksell Stereotactic System® overview" datasheet. Elekta AB, Stockholm, Sweden, Sep. 2010; 22 pages.
"microTargeting™ STar™ Drive System, Directions for Use," datasheet. FHC, Inc., Bowdoin, ME, Rev. C0, Oct. 2010; 49 pages.
"Micro Serrefines," datasheet [online]. Fine Science Tools, Foster City, CA, [retrieved on Dec. 30, 2011]. Retrieved from the Internet:<URL: http://www.finescience.com/Special-Pages/Products.aspx?ProductId=272; 1 page.
"Schwartz Micro Serrefines" datasheet [online]. Fine Science Tools, Foster City, CA, [retrieved on Dec. 30, 2011]. Retrieved from the Internet:<URL: http://www.finescience.com/Special-Pages/Products.aspx?ProductId=278&CategoryId=82>; 1 page.

* cited by examiner

RETAINER FOR IMMOBILIZING AN IMPLANTED CATHETER DURING STYLET RETRACTION, AND STYLET HOLDER FOR USE WITH SAME

RELATED APPLICATION(S)

This application claims the benefit of U.S. Provisional Application No. 61/389,910, filed Oct. 5, 2010, the content of which is incorporated herein by reference in its entirety.

TECHNICAL FIELD

Embodiments of the present invention relate generally to medical devices and, more particularly, to retainer systems and methods for immobilizing or restraining a catheter (e.g., an implanted brain infusion catheter) while a stylet is being extracted from the catheter, and to stylet holders operable to selectively grip and retain a stylet.

BACKGROUND

Use of a catheter to deliver a therapeutic agent to the brain (e.g., into the intracerebroventricular (ICV), intrathecal, or intraparenchymal (IPA) space) generally involves the insertion of the catheter into the cranial cavity via a burr hole. The catheter may be inserted until a therapy delivering catheter tip is positioned at a predetermined target site, after which the therapeutic agent may be dispensed through the catheter in accordance with a desired therapy profile.

During a typical implantation procedure, an incision is made in the scalp to expose the patient's skull. After forming the burr hole through the skull, the catheter may be inserted into the brain. To accurately place the catheter, clinicians may use stereotactic apparatus/procedures in a process referred to as framed stereotaxy. In framed stereotaxy, a ring-like frame is mounted to the patient's skull by pins or screws. The ring-like frame is then used to determine a three-dimensional data set, from which coordinates for the target site may be calculated. Various components and instruments may be utilized with the stereotactic apparatus to assist in guiding the catheter tip to the target site.

Depending on the stiffness of the catheter, a stylet may be utilized to permit the clinician to adequately push the catheter into the body. Typically, a stylet is constructed as a slender rod of relatively stiff but flexible material. The stylet may be inserted into a proximal end of the catheter until it abuts or otherwise contacts an engagement surface within the catheter near the catheter's distal end. The stylet may then be used to push the catheter until the distal end of the catheter is at the desired target site.

Once the catheter tip is implanted at the target site, the stylet may be withdrawn from a proximal end of the catheter (i.e., the end that remains outside of the skull). The catheter may then be anchored relative to the burr hole, e.g., via a burr hole anchor surgically attached to the skull. An end of the protruding portion of the catheter may then be connected, often via a secondary catheter, to a reservoir containing the therapeutic agent. After the secondary catheter is connected and tunneled beneath the skin to the reservoir, the scalp incision(s) may be closed and the system may deliver therapy in accordance with the desired profile.

To provide the desired stylet rigidity, an outer diameter of the stylet may be sized to fit tightly within the catheter. As one can appreciate, extraction of such a stylet may result in unintended pulling or displacement of the catheter, and therefore movement of the catheter's therapy-delivering tip, from its desired location (such displacement may be caused by a variety of factors including, for example, frictional and/or suction forces between the stylet and catheter, both of which may be amplified by the use of a relatively soft catheter material). Stated alternatively, the process of physically extracting the stylet from the catheter may inadvertently (e.g., via frictional interaction with the catheter) impart forces that are capable of displacing the catheter tip relative to the target site. Depending on the application, even slight displacement of the tip may result in reduced therapeutic efficacy.

Moreover, in some applications, the stylet may be attached to various structure, e.g., to part of the stereotactic frame, to hold the stylet stationary and/or to assist with its insertion into and/or removal from the catheter. Depending on the construction and material of the stylet, such attachment may present problems. For example, where a set screw or the like is used to contact and restrain the stylet, inherent variability in clinician actuation of the set screw may result in under- or over-tightening of the set screw, the former potentially resulting in inadequate anchoring, while the latter may potentially damage the stylet.

SUMMARY

The present invention may overcome these and other issues with prior devices, systems, and methods by, in one embodiment, providing a system for immobilizing a catheter during extraction of a stylet located within a lumen of the catheter while at least a portion of the catheter is implanted in tissue. The system includes a cannula defining a cannula lumen configured to slidably receive therein the catheter and the stylet, wherein the cannula further includes a first end. The system also includes a retainer configured to engage the first end of the cannula such that the retainer is restrained from longitudinal movement relative to the cannula. The retainer defines one or more surfaces configured to restrain longitudinal movement of the catheter relative to the retainer, the one or more surfaces further defining an opening sized to allow passage of the stylet through the retainer.

In another embodiment, a method for withdrawing a stylet from a lumen of a catheter is provided, wherein the method includes: positioning the catheter containing the stylet therein through a lumen of an elongate guide cannula; securing the guide cannula to a surgical apparatus to immobilize the guide cannula; and attaching a retainer to a proximal end of the guide cannula to longitudinally restrain the retainer relative to the guide cannula. The retainer includes a restraining surface defining an opening through which the stylet extends. The method further includes: withdrawing the stylet from the catheter through the opening; and restraining movement of the catheter relative to the guide cannula with the restraining surface of the retainer.

In yet another embodiment, a stylet holder is provided including a body having formed therein both a recess configured to receive a portion of a stylet, and a passageway intersecting the recess. A plunger is also provided and configured to translate within the passageway. A biasing member is provided and operatively positioned between the plunger and the body, the biasing member configured to bias the plunger towards the recess.

The above summary is not intended to describe each embodiment or every implementation of the present invention. Rather, a more complete understanding of the invention will become apparent and appreciated by reference to the following Detailed Description of Exemplary Embodiments and claims in view of the accompanying figures of the drawing.

BRIEF DESCRIPTION OF THE VIEWS OF THE DRAWING

The present invention will be further described with reference to the figures of the drawing, wherein:

FIG. 3A-3B are perspective views of the cannula system of FIG. 2 with various structure removed for clarity, wherein: FIG. 3A illustrates the system during catheter insertion into a guide cannula; and FIG. 3B illustrates the system after partial retraction of the guide cannula, wherein a catheter retainer in accordance with one embodiment of the invention is shown in FIG. 3B holding the catheter relative to the guide cannula for stylet extraction;

FIGS. 5A-5B illustrate a catheter retainer in accordance with another embodiment of the present invention, wherein: FIG. 5A is a perspective view of the retainer before attachment to the guide cannula; and FIG. 5B is a partial section view of the retainer of FIG. 5A once attached to the guide cannula;

Figure 1:
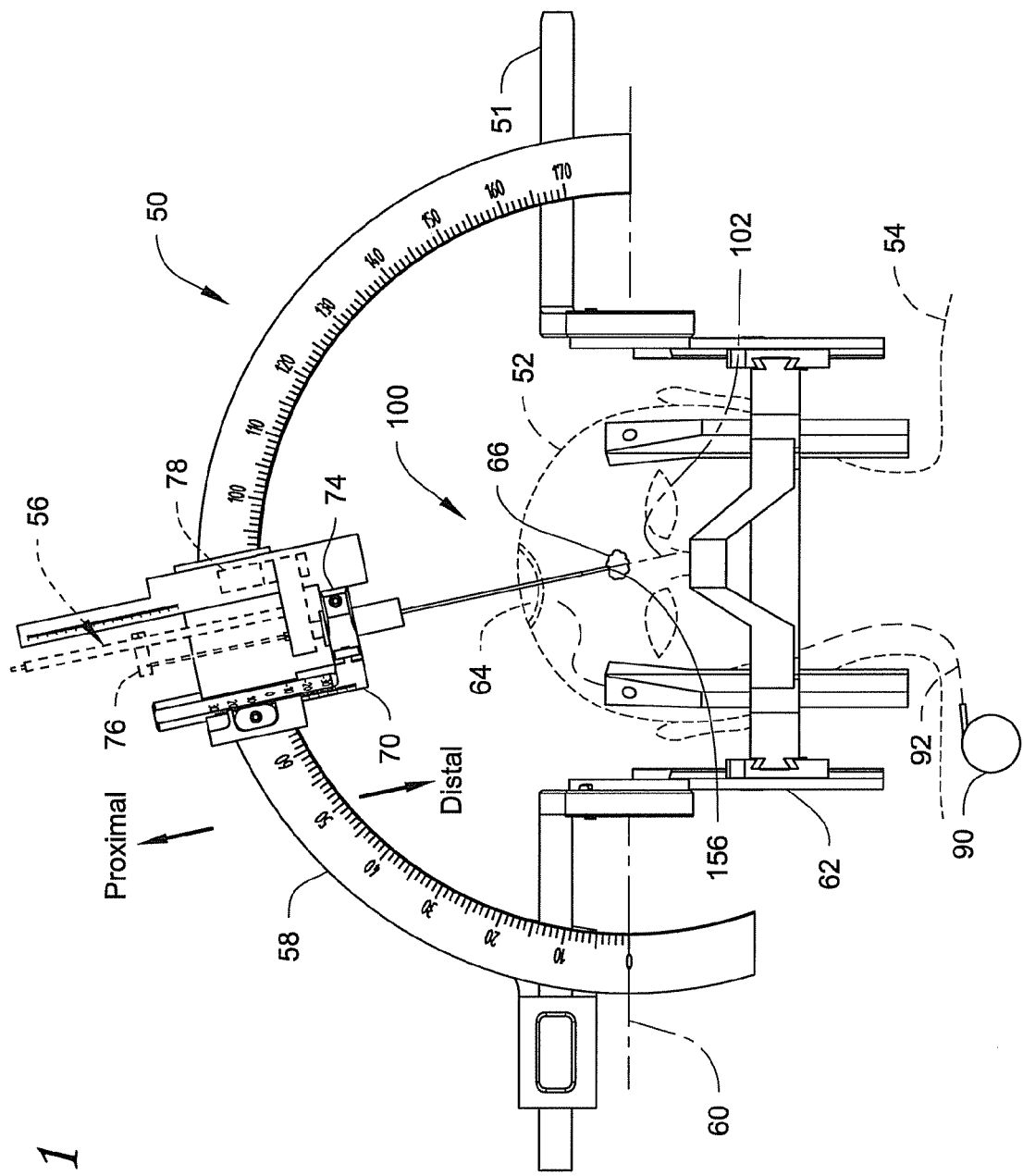
FIG. 1 is a diagrammatic perspective view of an exemplary cannula system and catheter delivery system in accordance with embodiments of the present invention, the system shown in conjunction with a stereotactic frame attached to a patient's head.

The figures are rendered primarily for clarity and, as a result, are not necessarily drawn to scale. Moreover, various structure/components, including but not limited to fasteners, bearings, electrical components (wiring, cables, etc.), fluid components, and the like, may be shown diagrammatically or removed from some or all of the views to better illustrate aspects of the depicted embodiments, or where inclusion of such structure/components is not necessary to an understanding of the various exemplary embodiments of the invention. The lack of illustration/description of such structure/components in a particular figure is, however, not to be interpreted as limiting the scope of the invention in any way.

DETAILED DESCRIPTION OF EXEMPLARY EMBODIMENTS

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

Embodiments of the instant invention may be directed to medical systems and devices, as well as to procedures for using the same. For instance, one embodiment of the invention is directed to a catheter delivery or cannula system for implanting and/or positioning a distal tip of a catheter at a target site in three-dimensional space (e.g., within a human or other mammalian body), and immobilizing the catheter while a stylet positioned within the catheter is subsequently extracted. In the illustrated embodiment, exemplary systems and methods are described and illustrated in the context of a brain therapy catheter implanted into tissue within a skull cavity, e.g., through a burr hole formed in skull tissue. Exemplary cannula systems may then be used to immobilize the catheter, i.e., minimize or prevent movement of the distal catheter tip, while a stylet used to insert the catheter is subsequently extracted or removed from a lumen of the catheter. However, this particular scenario is not limiting as other implantations e.g., implantation through other portals, are contemplated without departing from the scope of the invention. Additionally, embodiments of the invention may also provide stylet holders and systems configured to selectively engage and hold the stylet by application of a repeatable clamping or frictional force applied to the stylet. Stylet holders in accordance with embodiments of the present invention may avoid the variability often associated with conventional set screw engagement configurations.

FIG. 1 illustrates a cannula system 100 in accordance with one embodiment of the present invention. As illustrated in this view, the system 100 may optionally be utilized with a separate surgical structure or apparatus, e.g., stereotactic system 50, as is known in the art (see, e.g., a Leksell stereotactic system distributed by Elekta AB of Stockholm, Sweden; or a CRW stereotactic system distributed by Integra Radionics, Inc. of Burlington, Mass., USA). The stereotactic system 50 may include a frame 51 fixedly attached to the head or skull 52 of a patient 54 and positioned relative to a burr hole 64 formed through the skull. The cannula system may optionally include a drive member or drive system to which various surgical instruments may be attached. The drive member may be configured to selectively translate an elongate surgical instrument into and out of the skull 52 through the burr hole 64. While illustrated herein as using the stereotactic system 50 and drive member, cannula systems in accordance with embodiments of the present invention may be used without these items, or may be used with other surgical apparatus/placement systems, without departing from the scope of the invention.

An exemplary stereotactic frame 51 may include an arc-shaped guide 58 along which a mount 70 may be adjustably positioned. The arc-shaped guide 58 may move, e.g., pivot about a transverse pivot axis 60, relative to a mounting portion 62 of the frame 51 (the mounting portion being fixed to the skull). As a result of this construction, the mount 70 may position and align the surgical instrument to reach most any location in localized three-dimensional space within the skull 52.

During an exemplary surgical procedure, an incision may be made in the scalp and a portal, e.g., the burr hole 64, may be formed within the skull 52. The burr hole 64 may be located based upon a previously determined location of a target site 66 to which therapy is to be administered such that the burr hole (and its associated anchor) is aligned with the target site. The approximate location of the target site 66 may be determined based upon various imaging (e.g., CT, MRI) and mapping techniques as are known in the art. A burr hole anchor (not shown) may be used to secure the instrument (e.g., a therapy delivery device such as a catheter 156

(described in more detail below)) relative to the burr hole 64 after implantation. The catheter may ultimately be connected to a therapeutic source, e.g., an implantable infusion pump 90, via a secondary catheter 92.

As used herein, relative terms such as "left," "right," "fore," "forward," "aft," "rearward," "top," "bottom," "upper," "lower," "above," "below," "horizontal," "vertical," and the like are, unless otherwise stated, from the perspective shown in the particular figure. These terms are used herein to simplify the description, however, and not to limit the scope of the invention in any way. Similarly, the relative terms "proximal" and "distal" may be used herein to describe various aspects of the components of the system. Where so used, these terms are defined from the perspective of a clinician, i.e., "proximal" indicates a direction or portion of the particular component/system that is positioned (or intended to be positioned) outside or towards the outside of the skull, while "distal" refers to a direction or portion that is at or more near (or intended to be at or more near) the predetermined target site 66.

Once the target site 66 is located and the burr hole 64 is formed, the guide 58 and stationary mount 70 may be adjusted such that the mount 70 is generally aligned with the burr hole and the target site 66. Once so located, the mount 70 may be generally fixed in place, e.g., fixed so as to restrict movement of the mount along the guide 58 and about the axis 60, by fasteners or the like. At this point, the catheter 156 may be delivered, via the burr hole, to the target site 66. In one embodiment, such delivery may occur by manual insertion controlled by the clinician. In alternative embodiments, catheter delivery may be at least partially automated with the use of the optional drive member, e.g., a microdrive 56. An exemplary microdrive 56 may be similar in some respects to a deep brain stimulation (DBS) microdrive, see, e.g., the "microTargeting Drive System for Stereotactic Positioning" distributed by FHC Inc., of Bowdoin, Me., USA. Once again, while portions of the following description make reference to the use of a microdrive 56, such use is optional, i.e., manual catheter insertion methods are also within the scope of the invention.

Figure 2:
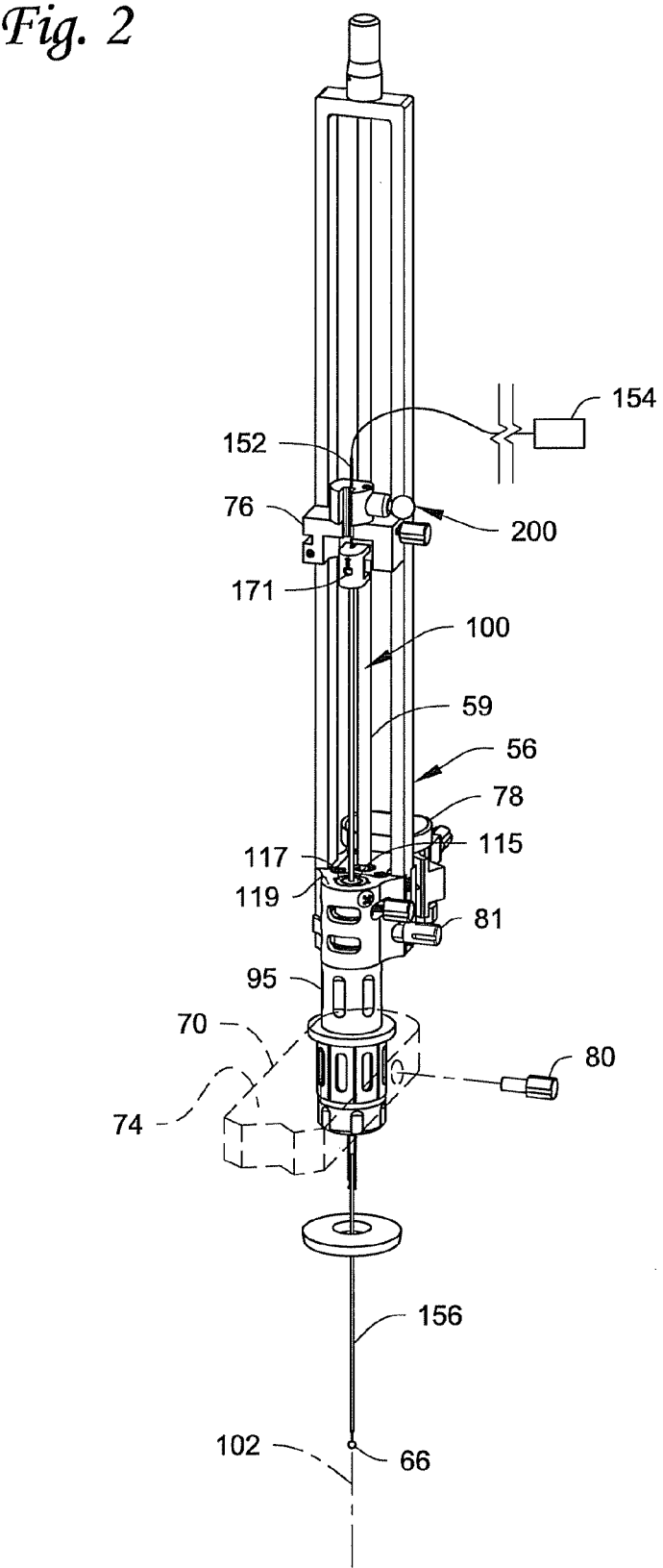
FIG. 2 is an enlarged perspective view of the cannula system of FIG. 1 as utilized with an optional drive system and optional infusion system, the cannula system illustrated with a catheter retainer and a stylet holder both in accordance with embodiments of the instant invention.

FIG. 2 illustrates an enlarged view of the cannula system 100 and optional microdrive 56 (with various structure, e.g., the stereotactic frame, removed for clarity). As shown in this view, the microdrive 56 may be attached to the mount 70 (see also FIG. 1) of the stereotactic system 50 with an adapter 95. Various adapters 95 may permit attachment of the cannula system 100 to a variety of stereotactic systems (e.g., the Leksell or CRW systems). As illustrated in FIG. 2, the adapter 95 may be placed within an opening formed in a fixed platform 74 of the mount 70 and secured in place, e.g., with a fastener (e.g., a thumb screw 80) or via the adapter incorporating an expandable collet (e.g., a lower portion of the adapter may thread into an upper portion, causing the upper portion to expand within the opening of the platform). The microdrive 56 may be secured relative to the adapter with a fastener (e.g., thumbscrew 81). The adapter 95 may include locating features to ensure complete engagement of the adapter to the platform 74, and the adapter to the microdrive 56.

The adapter 95 may define a frame stop surface 117 that is located a predetermined distance from the platform 74 when the adapter is correctly installed. Once the adapter 95 is accurately affixed to the mount 70, the stereotactic system 50 may define a first portion, e.g., the fixed platform 74 (see, e.g., FIGS. 1 and 2), to receive and hold instruments (as well as a base of the optional microdrive) in a fixed relationship relative to the target site 66.

In configurations incorporating the optional microdrive 56, the system 50 may also define a second portion, e.g., a carrier platform 76, to also receive and hold various instruments such as a stylet 152 via a stylet holder 200. As further explained herein, the carrier platform 76 may be selectively movable, e.g., translatable along a drive screw 59, relative to the first portion (fixed platform 74) to selectively advance or withdraw an instrument (the stylet 152) effectively attached to the carrier platform. In the illustrated embodiment, the carrier platform 76 may be advanced or withdrawn by a motor 78 (diagrammatically illustrated in FIG. 2). As a result, the cannula system 100 may, via the microdrive 56, provide for precisely controlled insertion and withdrawal of the stylet 152. Once again, however, the microdrive 56 is optional and, as such, may not be included with other embodiments of cannula systems of the present invention. Further details regarding other aspects of the cannula system may be described in detail in U.S. patent application Ser. No. 13/247,149, entitled Cannula System and Method for Immobilizing an Implanted Catheter during Catheter Anchoring, filed on the same day herewith, the content of which is incorporated herein by reference in its entirety.

Figure 3A:
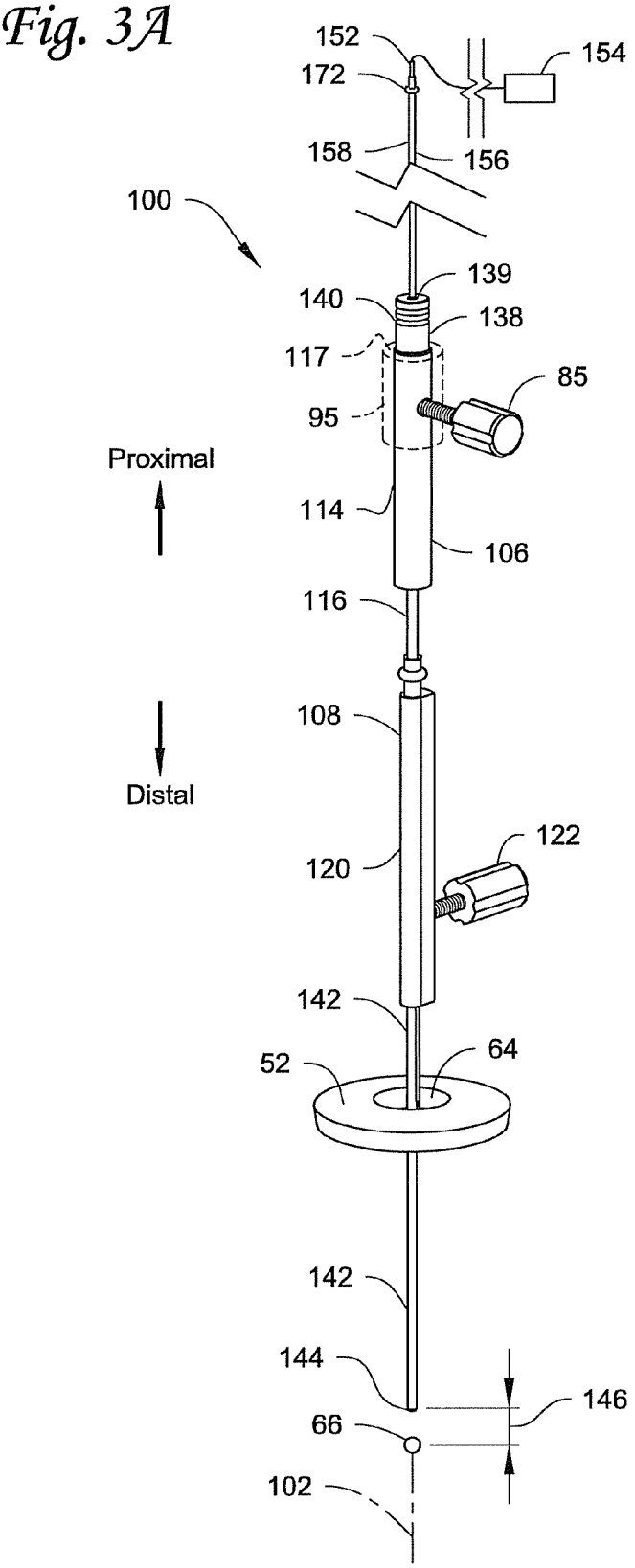
Figure 3B:
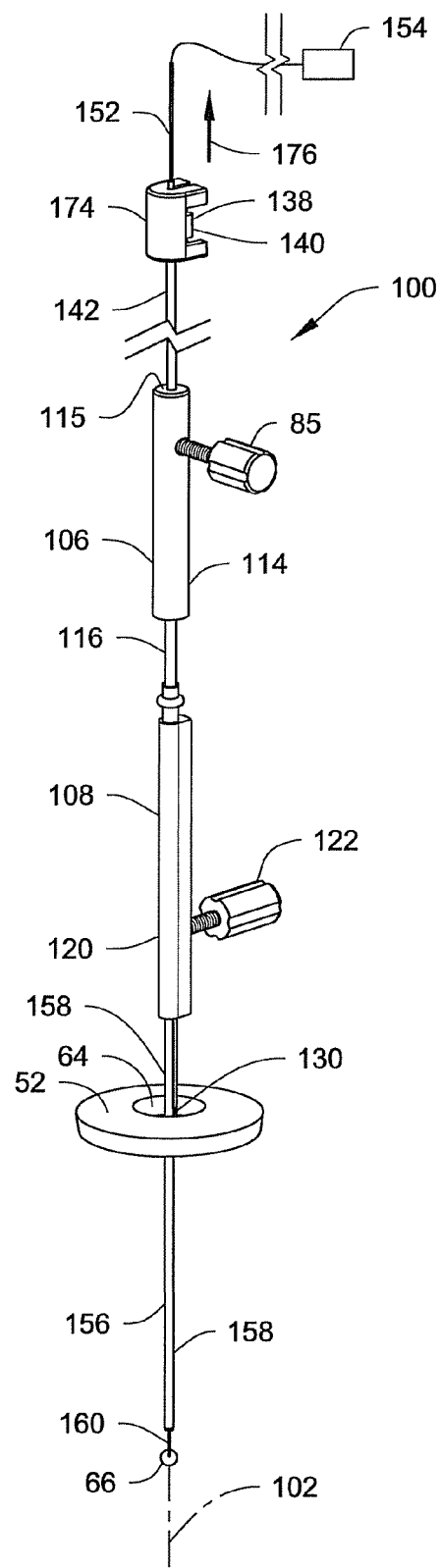

FIGS. 3A and 3B are perspective views of the exemplary cannula system 100 with some structure removed for clarity. As shown in these views, the exemplary cannula system 100 may include a cannula, e.g., an elongate guide cannula 138, and a catheter retainer 174 (see FIG. 3B) in accordance with embodiments of the present invention. In some embodiments, the system 100 may also include a catheter (e.g., a needle tip catheter 156), and the stylet 152 for use in pushing the catheter through the guide cannula 138. In the particular illustrative embodiment of FIGS. 3A-3B, the system 100 may be used with, or otherwise include, a frame guide tube 106 and an elongate cinch tube 108. The guide cannula 138 and catheter retainer 174 are described in more detail below, as are exemplary methods for using the system 100.

While not necessary to an understanding of the invention, the guide tube 106 may include a body 114 and an elongate tubular extension 116 protruding or extending from the body, e.g., extending towards the target site 66. The body 114 may be configured to be fixed or securely retained relative to a surgical structure or apparatus located outside the burr hole, e.g., fixed relative to the adapter 95 (shown diagrammatically only in FIG. 3A) and thus relative to the fixed platform 74 (see FIG. 2). Although other configurations are certainly possible, an upper surface 115 of the body 114 (see FIG. 3B) may be configured to align with the frame stop surface 117 (see FIG. 3A), which in the illustrated embodiment, is defined by an upper surface of the adapter 95 (which may also align with the surface 119 of the microdrive 56 as indicated in FIG. 2). The body 114 may be fixed relative to the adapter 95, e.g., via a thumb screw or the like. In the illustrated embodiment, the guide tube 108 may remain fixed relative to the stereotactic system 50 (or other external apparatus) during the entire implantation procedure. Moreover, the distance from the frame stop surface 117 to the target site 66, once fixed, may remain constant throughout the implantation procedure.

Notwithstanding this fixed relationship; the cinch tube 108 may be longitudinally adjusted or displaced relative to the guide tube 106, e.g., along the tubular extension 116 of the guide tube. For instance, the body 120 of the cinch tube 108 may include a retaining or lock member, e.g., threaded fastener 122, that threads into an aperture on the cinch tube body and, when tightened, engages an outer surface of the tubular extension 116 to secure the cinch tube relative to the guide tube 106 at one or more longitudinal locations. By loosening the fastener 122, the cinch tube 108 may be relocated longitudinally along the guide tube 106, where it may be retightened upon reaching the desired position. Regardless of the relative location of the cinch tube 108, the guide tube 106 and the cinch tube remain aligned with a longitudinal axis 102 of the cannula system 100 throughout the implantation procedure. Moreover, once the cinch tube 108 is located in the desired position, it may stay fixed for the remainder of the implantation procedure. The cinch tube 108 and guide tube 106, as well as a procedure for use of the same, are described in more detail in U.S. patent application Ser. No. 13/247,149.

With this general description, exemplary methods for implanting a catheter using a stylet and immobilizing the catheter during stylet retraction will now be described. Where beneficial, other mechanical/structural aspects and components of various embodiments of the cannula system 100 will also be described.

FIGS. 3A and 3B illustrate the exemplary cannula system 100 after formation of the burr hole 64 through the skull 52. These and subsequent figures represent a surgical configuration after the stereotactic system 50 (see FIG. 1) is in place, the guide tube 106 has been secured (i.e., fixed in place) within the adapter 95 and the fixed platform 74 (see also FIG. 2), and the cinch tube 108 has been secured at the desired location relative to the guide tube 106. Once again, to better illustrate the cannula system 100, some structure, e.g., the stereotactic system 50, may be removed from these and subsequent views.

While not illustrated in FIGS. 3A and 3B, a burr hole anchor (not shown) may be attached to the skull at the burr hole 64 prior to the positioning of the cinch tube 108 for subsequent anchoring of the catheter 156. While a variety of burr hole anchor configurations are suitable, the anchor may, in one embodiment, be configured in accordance with embodiments shown and described in U.S. patent application Ser. No. 12/357,120 (U.S. Pat. App. Pub. No. 2009-0187149-A1), incorporated herein by reference in its entirety.

In one embodiment, the catheter 156 may be implanted by inserting a distal end of the catheter 156, with the stylet 152 inserted into the catheter, into a first or proximal end of the guide cannula 138. The guide cannula may assist in directing the catheter 156 to the target site 66. The guide cannula 138 may include a flange or head 140 (e.g., at a first or proximal end) and a tubular body 142 extending towards the target site 66 (see also FIG. 4). A cannula lumen or passageway 139 (see FIG. 5B) may be formed completely through the cannula 138 (e.g., through the head and tubular body) so that the catheter may be slidably received within the guide cannula and pass from the proximal end of the cannula through its distal end. In the illustrated embodiment, the tubular body 142 of the guide cannula 138 may have a body length selected to place its inserted distal tip 144 near, e.g., at a preset distance 146 from, the target site 66 when the head 140 abuts the surfaces 115/117 as shown in FIG. 3A. While not shown, a removable obturator insertable into the guide cannula 138 may be used to assist in first inserting the guide cannula.

Once the guide cannula 138 is fully inserted (e.g., when the head 140 rests against the surface 115/117), the guide cannula may be secured in place relative to the guide tube 106 and stereotactic frame (e.g., with a thumb screw 85 or the like passing through an opening in the guide tube 106).

A "wet" infusion is illustrated in the embodiment of FIGS. 3A-3B. In wet infusion, an infusion source may deliver an infusing fluid to the stylet during at least part of the implantation. Accordingly, a proximal end of the hollow tubular stylet 152 may be connected to a pressurized infusion source 154 such as a syringe pump (e.g., a model PHD 2000 Harvard Apparatus pump distributed by Instech Laboratories, Inc. of Plymouth Meeting, Pa., USA) to prime and maintain a constant infusing flow of fluid, e.g., phosphate buffered saline (PBS) fluid, through the stylet. An opposite or distal end of the stylet may then be inserted into a proximal end of the catheter 156. While the flow rate through the stylet 152 may vary, it is, in one embodiment, maintained at about 2 to about 10 micro liters/minute (µl/min), e.g., about 5 ml/min.

The needle tip catheter 156 may, in one embodiment, be configured in accordance with embodiments described and illustrated in U.S. patent application Ser. No. 12/276,794 (U.S. Pat. App. Pub. No. 2009-0143764-A1), incorporated herein by reference in its entirety. The catheter 156 may thus include a flexible (e.g., urethane) body 158 and a rigid needle tip 160 (see FIG. 3B).

The infusing stylet 152 may be manually inserted into the catheter 156 until a distal tip of the stylet abuts an internal portion or surface of the catheter. The assembled stylet and catheter may then be manually inserted into the guide cannula 138 (which, in the illustrated embodiment, is itself inserted through both the guide tube 106 and cinch tube 108 as shown in FIG. 3A). The stylet 152 may be sufficiently rigid to permit pushing of the catheter 156 through the lumen of the guide cannula 138 by application of a force applied to the stylet at its upper or proximal end, thereby effectively allowing positioning of the distal tip of the catheter through the guide cannula.

In the illustrated embodiment, infusing of the stylet 152 may continue as the stylet and catheter are inserted through the guide cannula 138. This may ensure that a continuous positive flow of PBS fluid out of the distal tip of the catheter is maintained during catheter positioning. During this process, some PBS fluid may escape at the interface between the distal tip of the stylet and the contact area (not shown) within the catheter 156. To prevent this fluid from leaking upwardly through the annular region between the catheter and the stylet, a constricting or sealing member may be provided near the upper (proximal) end of the catheter. In the illustrated embodiment, the sealing member may be configured as an O-ring 172 as shown in FIG. 3A that is placed around the catheter body to compress and seal the generally elastic catheter body 158 against the more rigid outer surface of the stylet 152. By accurate sizing of the O-ring 172, a sufficient radial sealing force may be provided that reduces or eliminates fluid leakage out of the annular space between the catheter and the stylet.

By continuing to infuse the stylet 152 (and accompanying catheter 156), a constant positive pressure (and thus positive flow) through the catheter may be maintained during implantation, potentially preventing blood and other fluids from entering the distal tip of the catheter. While such a configuration provides potential benefits, the infusion source 154, corresponding infusing flow, and the O-ring may be eliminated in other (e.g., non-wet) applications without departing from the scope of the invention.

With the catheter 156 located as shown in FIG. 3A, the stylet 152 may be displaced downwardly into the tissue (e.g., towards the target site 66). In one embodiment, this displacement of the stylet and catheter may be achieved by attaching the stylet to the microdrive 56, e.g., to the motorized carrier platform 76 (see FIG. 2), using the stylet holder 200 as further described below. The clinician may then actuate the motor 78 (see, e.g., FIGS. 1 and 2) to drive the stylet 152 and catheter 156 downwardly the remaining distance (e.g., the preset difference 146) to the catheter's intended location (e.g., until the needle tip 156 is at the target site 66 as shown in FIG. 3B) at a controlled rate. In one embodiment, the descent rate is about one mm/minute, although other rates are certainly possible. Alternatively, the stylet may be manually displaced by the clinician.

Once the needle tip 160 of the catheter 156 is at the target site 66 as shown in FIG. 3B, the guide cannula 138 may be manually raised (while holding the stylet 152 and catheter 156 stationary, e.g., by loosening the thumb screw 85. In one embodiment, the guide cannula may be retracted until it contacts the O-ring 172. The guide cannula 138 may then, once again, be secured to surgical apparatus or frame structure, e.g., the stereotactic frame, to immobilize the guide cannula at this new location relative to the fixed platform 74 (e.g., using the thumb screw 85).

Figure 4:
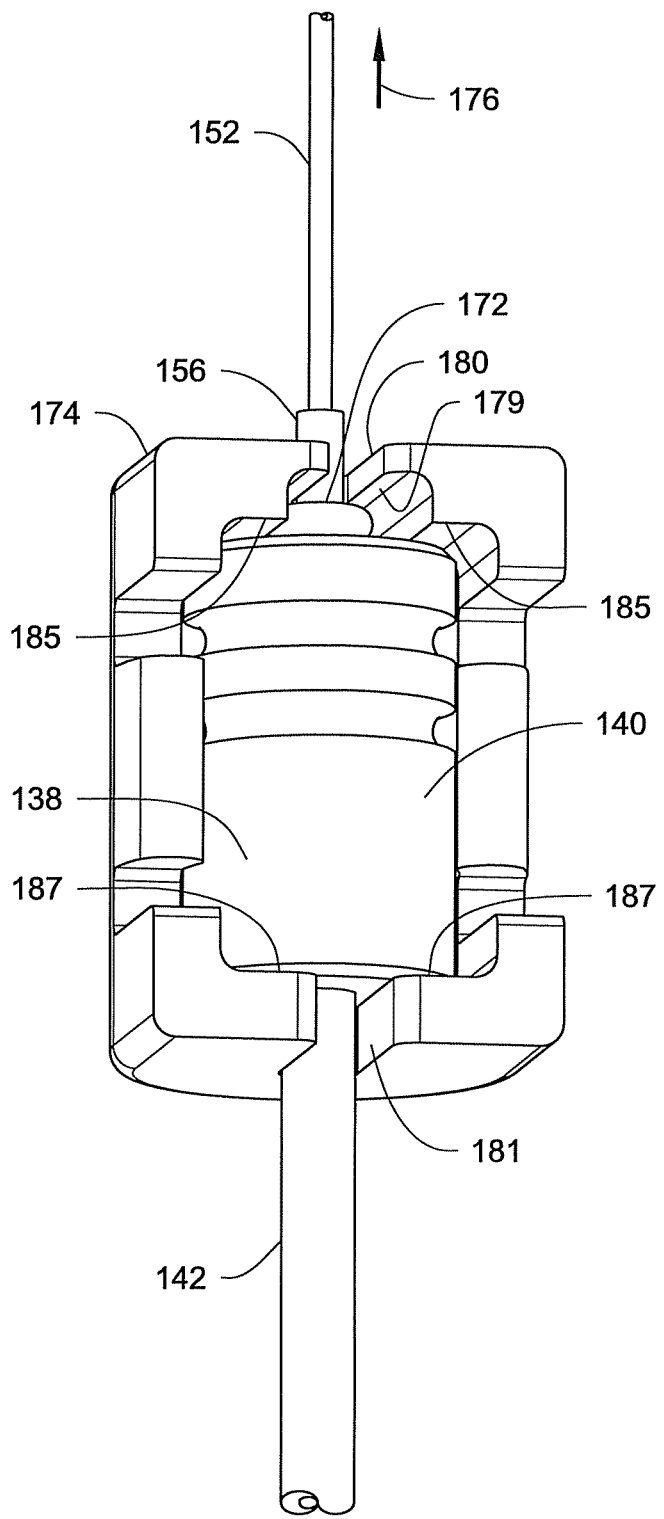
FIG. 4 illustrates an opposite perspective view of the catheter retainer of FIG. 3B.

With the guide cannula 138 retracted and secured, the removable retainer 174 may now be attached to or engaged with the first proximal end (e.g., the flange or head 140) of the guide cannula (and the O-ring 172) as illustrated in FIGS. 3B and 4. When so engaged, the retainer 174 may be restrained from longitudinal movement relative to the guide cannula (e.g., little or no relative longitudinal movement may occur between the retainer and guide cannula). Moreover, the retainer 174 may define one or more restraining surfaces 179 configured to restrain longitudinal movement of the catheter 156, relative to the cannula 138 (and thus relative to the retainer 174), at least in a direction away from the target site 66. These restraining surfaces may further define an opening sized to allow passage or extension of the stylet 152 through the retainer. For example, the surfaces 179 may captivate the O-ring 172 (now acting as a friction member positioned about the catheter and located between the cannula and the surface 179, and between the retainer and the catheter) and restrict its movement relative to the head 140. As a result of O-ring friction with the catheter, the surfaces 179 of the retainer may also restrain longitudinal movement (at least in the proximal direction) of the catheter 156 relative to the retainer 174, and thus relative to the guide cannula (the latter which is, once again, secured to the fixed platform 74 via the screw 85), during retraction of the stylet 152.

In the illustrated embodiment, the retainer is side-loaded over the head 140 of the guide cannula 138 (e.g., attached from a direction transverse to the longitudinal axis of the guide cannula). As a result, the retainer 174 may be installed and removed without interference from other components in the system 100. To permit side loading, the retainer 174 may form a body defining a semi-cylindrically shaped recess configured to receive the cylindrically shaped flange or head 140 of the guide cannula 138. Further, the retainer 174 may define one or more openings, e.g., open-ended slots, configured to permit passage of the retainer over the head 140 with the catheter/stylet in place as shown in FIG. 4. In the illustrated embodiment, a first slot 180 is formed in the surface 179 and is defined by a slot width sized to receive the catheter 156 with slight clearance, but provide interference (e.g., via the surface 179) to longitudinal movement of the O-ring 172. A second slot 181 may be sized to receive the body 142 of the cannula 138 with minimal clearance as shown in FIG. 4. As a result, the head 140 may be placed within the recess of the retainer 174 by passing the flange through an open side of the retainer in a direction that is transverse to the longitudinal axis 102 of the guide cannula 138 (see FIGS. 3A-3B). As this occurs, the slots 180 and 181 may accommodate the catheter 156 and cannula body 142, respectively.

Figure 5A:
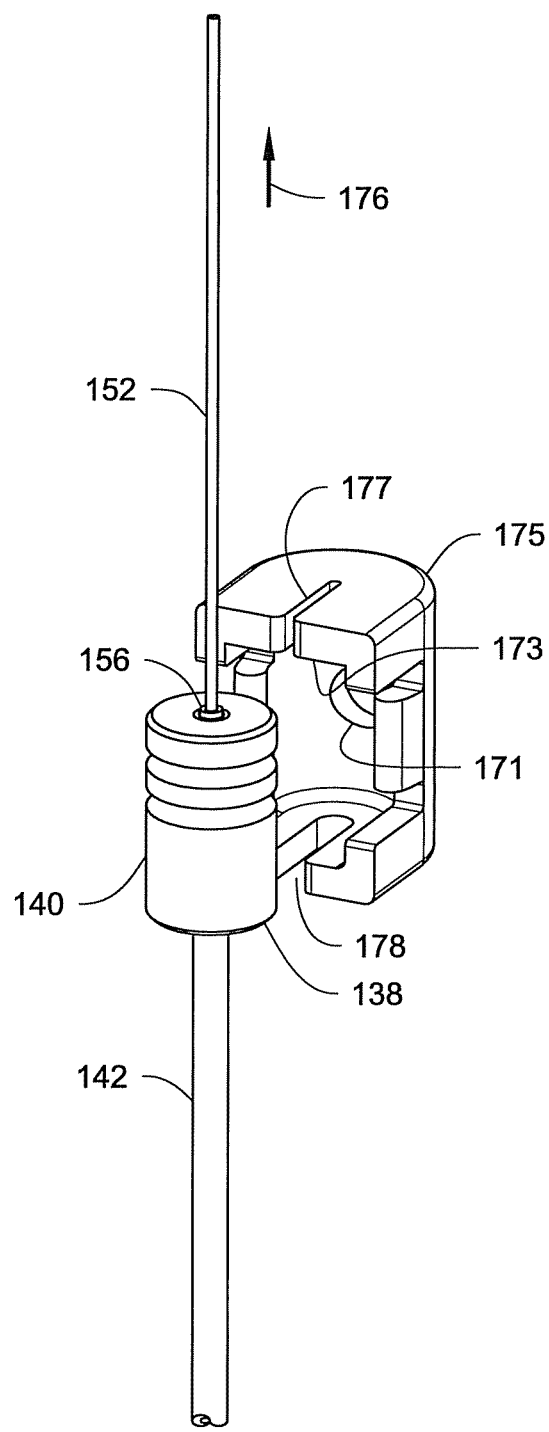
Figure 5B:
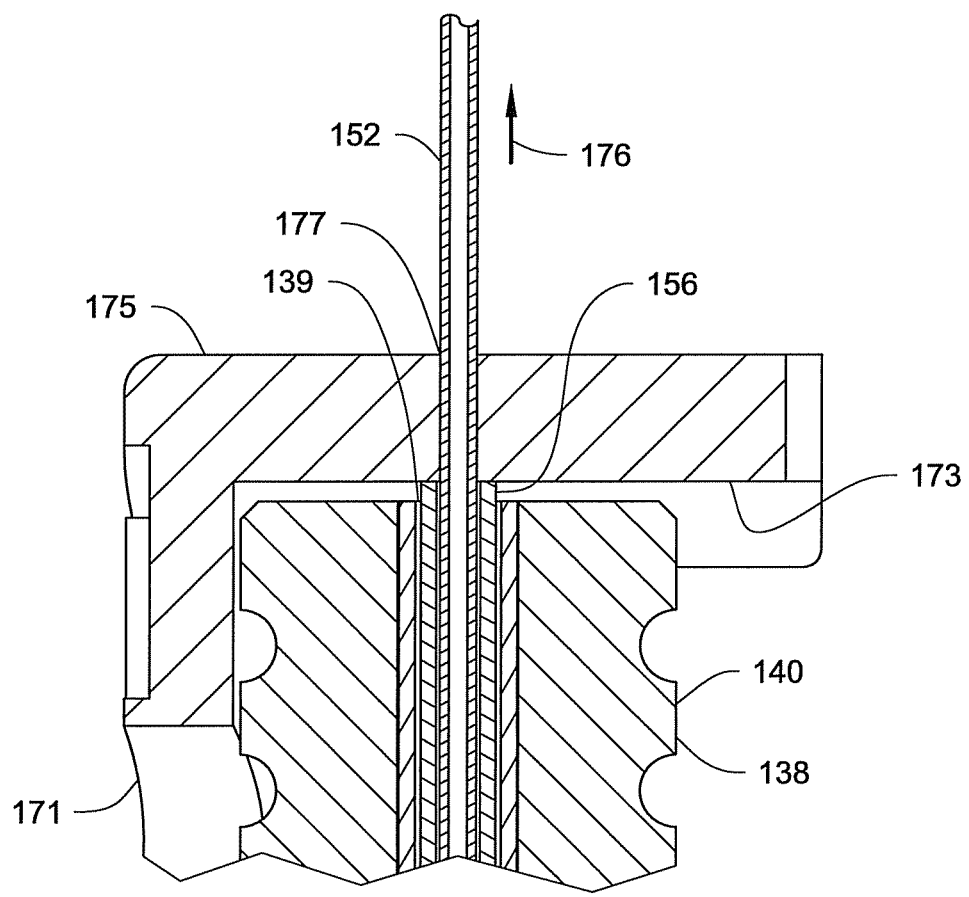

The configuration of the catheter retainer (e.g., dimensions, materials, etc.) may be selected to permit snap-fitting of the retainer to the head 140 of the guide cannula 138. For instance, as shown in FIG. 4, the retainer 174 may form protrusions or fingers 185 (top) and 187 (bottom) that engage and captivate the cannula head 140. In some embodiments, supporting the head 140 (e.g., with forceps) may be needed to avoid excessive bending of the cannula. Retainer removal may be accommodated by providing a hole 171 (see, e.g., FIGS. 2 and 5A) through which a forceps may be used to push the head 140 while holding the retainer. In one embodiment, the retainer is injection molded from medical grade thermoplastic such as Udell P-1700 polysulfone available from Solvay Advanced Polymers, LLC, of Alpharetta, Ga., USA.

With the catheter 156 now held fixed by the retainer 174, the stylet 152 may be withdrawn, e.g., moved in the direction 176 shown in FIGS. 3B and 4 through the opening or slot 180, either manually or by the motorized carrier platform 76 (see, e.g., FIG. 2). To ensure that additional fluid volume created within the catheter 156 as a result of stylet extraction does not interfere with positive flow of the PBS fluid out the catheter tip, the extraction rate of the stylet and the infusion rate of the PBS fluid may be set accordingly. Once the stylet reaches the desired retracted position, the infusion flow may continue at the same or a lesser rate to maintain positive PBS fluid flow.

While the embodiment of FIGS. 3A-4 utilizes the O-ring 172 to assist in sealing the annular space between the stylet and the catheter, it is contemplated that catheter retainers in accordance with other embodiments of the present invention may find application where such catheter/stylet sealing is not required. In such an embodiment, a retaining member 175 such as that illustrated in FIGS. 5A-5B may be utilized. Like the retaining member 174, the retaining member 175 may be side-loaded over the head 140 of the guide cannula 138 and may be similar in most respects to the retainer 174. For instance, the retainer 175 may include surfaces that engage the head 140 and define a first slot 177 and a second slot 178. The second slot 178 may be sized, once again, to accommodate receipt of the body 142 diameter of the guide cannula 138. However, the first slot 177 may, unlike the first slot 180 of the retainer 174, be sized to permit passage of only the stylet 152 (e.g., with zero or slight clearance), but sufficiently narrow so as to interfere or restrict passage/movement of the catheter 156 (the slot 177 width is smaller than an outer diameter of the body of the catheter). Stated alternatively, the retainer 175 may include a restraining surface 173 defining the first slot 177, wherein the restraining surface is operable to abut or contact a proximal, terminal end face of the catheter 156 as the stylet 152 is extracted. As a result, with the retainer 175 attached to the head 140 of the guide cannula 138, the stylet 152 may be extracted (moved in the direction 176) from the lumen of the catheter 156 without detrimental displacement of the catheter.

Accordingly, catheter retainers in accordance with embodiments of the present invention may longitudinally restrain a catheter (e.g., catheter 156) relative to the head of a guide cannula, which is in turn longitudinally restrained by its attachment to fixed structure (e.g., the platform 74). By providing catheter retainers that interact with a head of a guide cannula, variable depth placement of the catheter may be accommodated.

For stylet 152 attachment to, and detachment from, surgical apparatus, a stylet holder in accordance with embodiments of the present invention may be provided. An exemplary stylet holder is represented as item 200 in FIGS. 2 and 6-8. The stylet holder 200 may form part of a stylet holder system that further includes, e.g., the stylet 152 and other surgical hardware.

Stylets in accordance with embodiments of the present invention may be configured as relatively small cylindrical rods and may, as with the illustrative stylet 152, be hollow so as to permit infusion as described herein. The resulting relatively thin wall of such a stylet may be ill-suited to the variable and potentially crushing forces that could be applied by a conventional set screw arrangement. Stylet holders like the holder 200 described and illustrated herein may avoid the inherent variability in force applied by set screws by instead providing a biased plunger that may be manually withdrawn, but that engages the stylet with a consistent force when released.

Once again, while exemplary stylet holders are described in the context of the cannula system 100, other embodiments may find use in most any application that would benefit from a stylet holder that provides repeatable and consistent clamping loads.

Figure 6:
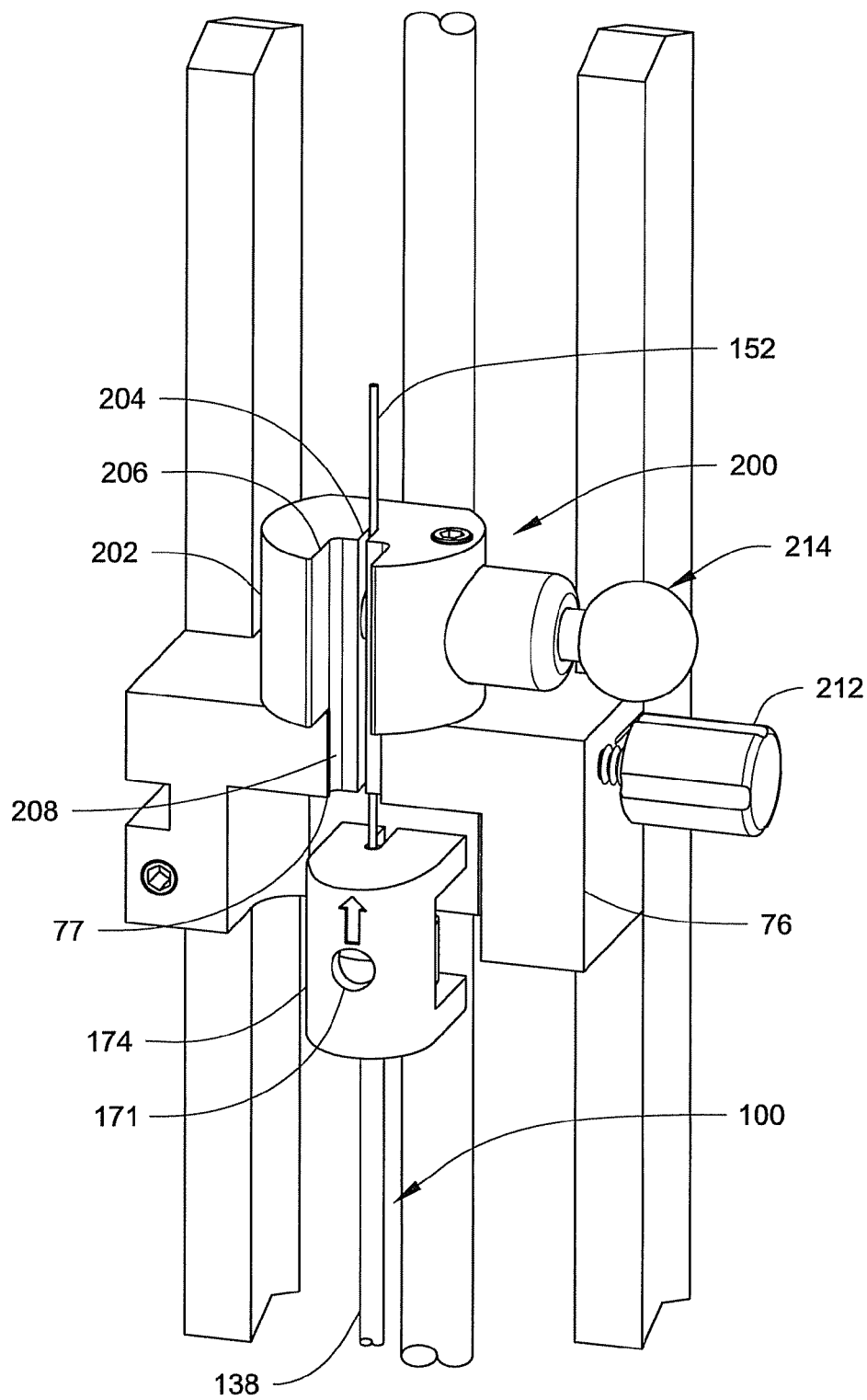
FIG. 6 is a perspective view of a stylet holder and system in accordance with one embodiment of the invention, the stylet holder shown during use with the cannula system of FIG. 2.

With reference to FIG. 6, the exemplary stylet holder 200 may include a body 202 having surfaces that define or form within the body a recess or slot 204 configured to receive a portion of the stylet 152. The slot 204 may permit side loading of a portion of the stylet with clearance during implantation procedures. The slot 204 may also provide an enlarged mouth 206 to assist with placing the stylet into the slot 204.

The body 202 may also include an engagement or attachment portion 208 that, in the illustrated embodiment, forms a protrusion that is received within an opening 77 in the surgical structure or apparatus (e.g., in the carrier platform 76) to secure the body 202 to the same. Once in place, a set screw 212 may be used to secure the body 202 relative to the platform 76. The body 202/platform 76 may include keying features to assist with aligning the body during insertion into the opening 77 of the platform 76.

Figure 7:
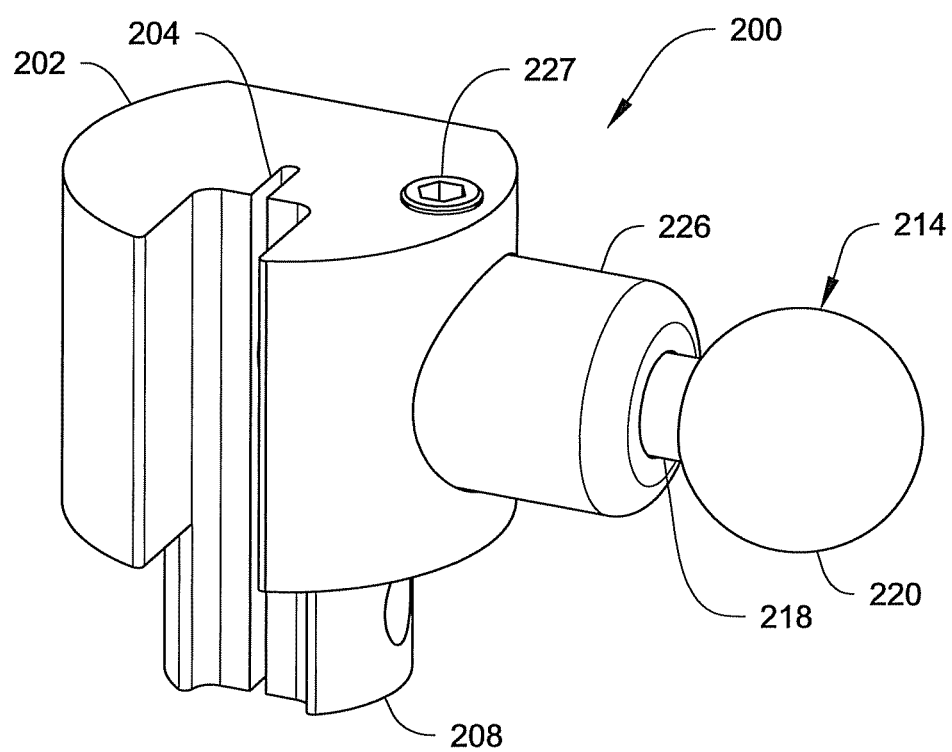
FIG. 7 is an enlarged view of the stylet holder of FIG. 6.

FIG. 7 illustrates the stylet holder 200 separated from the carrier platform 76. As shown in this view, the holder 200 may also include a plunger assembly 214 that, in the illustrated embodiment, is oriented transversely to the slot 204 for reasons that will become apparent.

Figure 8:
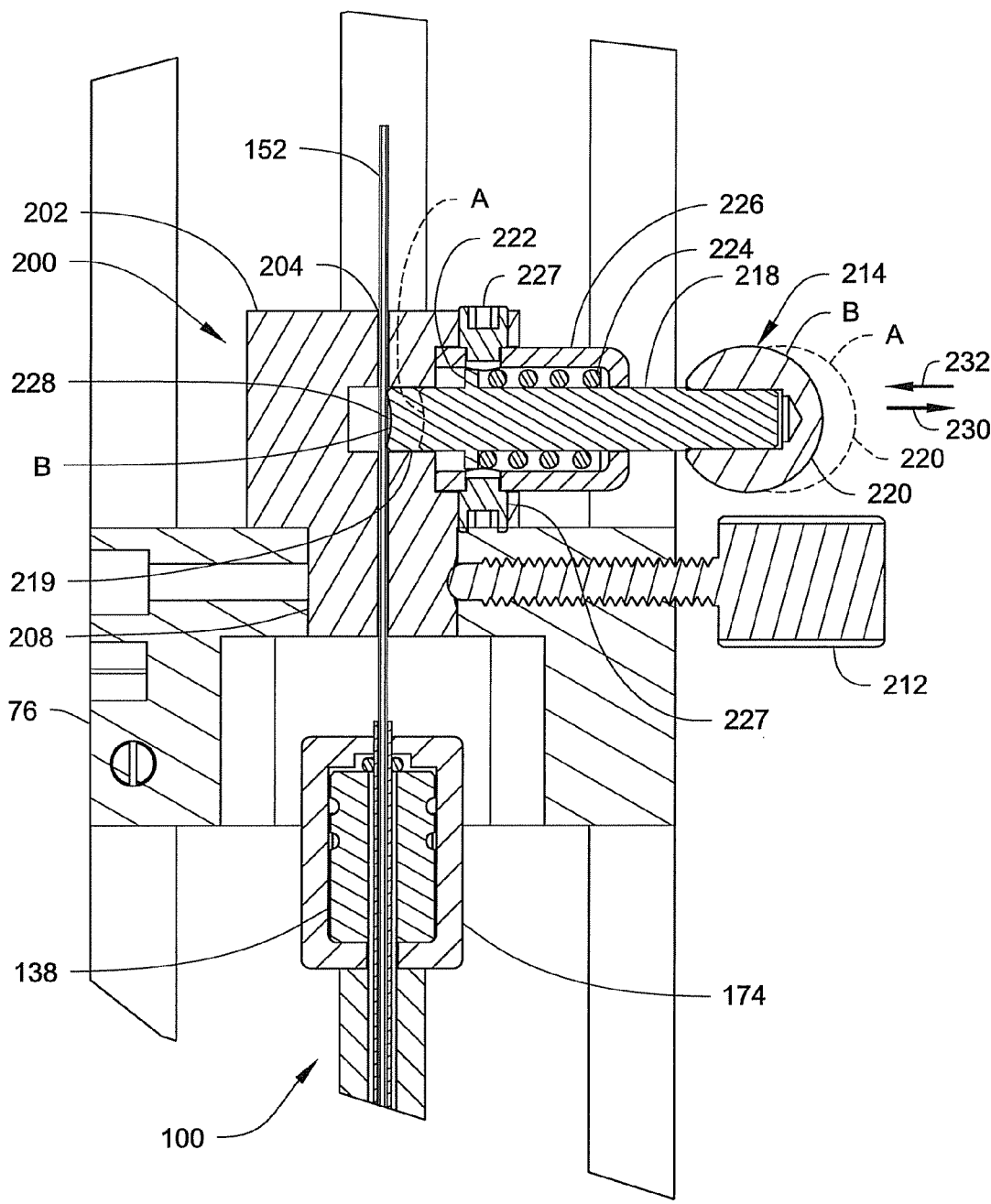
FIG. 8 is a section view of the stylet holder of FIG. 6.

FIG. 8 illustrates the stylet holder 200 and platform 76 in cross section. As shown in this view, the plunger assembly 214 may include: a shaft or plunger 218 located and translatable within a passageway 219 formed within the body 202; and an optional head 220. The passageway 219 may pass through a portion of the body and intersect the recess or slot 204 and, in the illustrated embodiment, pass completely through the slot as shown. The plunger 218 may include a flange 222 such that the plunger, in the illustrated embodiment, is biased towards the slot 204 by a biasing member, e.g., compression spring 224. To contain the spring and provide a reaction surface, the body may also include a housing 226 that is secured to the rest of the body via one or more set screws 227. The spring may thus be operatively positioned between the plunger and the body 202 (e.g., between the flange 222 and the housing 226).

The plunger may include a contact end 228 configured to contact and press against the stylet 152 and retain the stylet in place via friction. In the illustrated embodiment, the contact end 228 has a concave surface or profile to localize and direct the holding force applied by the plunger 218 to a relatively small contact area of the stylet. However, other contact end shapes are certainly possible without departing from the scope of the invention. Moreover, contact ends made of a material different than the plunger 218 are also contemplated. While the plunger 218, e.g., contact end 228, may be made of a variety of materials, it is in one embodiment, made of a rigid metal or plastic (e.g., polyetheretherketone (PEEK)).

In use, the clinician may grasp the plunger 218, e.g., via the head 220, and withdraw the plunger against the biasing force of the spring 224, e.g., pull the plunger in the direction indicated by arrow 230 to a first position A (represented in broken lines in FIG. 8). As the plunger is withdrawn, the contact end 228 moves to a location that is spaced-apart from the slot 204 and from the stylet 152. As a result, the stylet may be repositioned within the slot 204 (or inserted therein). Once the stylet 152 is located in the desired position, the clinician may release the plunger (e.g., the head 220), wherein the biasing force of the spring 224, acting between the flange 222 and an inside surface of the housing 226, causes the plunger 218 to move under biasing force towards the slot 204 in the direction 232, e.g., to a second position B (shown in solid lines in FIG. 8) wherein the contact end 228 abuts the stylet 152.

While various configurations are certainly possible, the spring 224 may, in one embodiment, be constructed of 0.48 millimeter (mm) diameter, 316 stainless steel wire having an outer coil diameter of about 4 mm to about 5 mm (e.g., about 5.3 mm). Such a spring may provide a force against the stylet of about 0.5 pounds (lbf) to about one lbf (about 2.2 Newtons (N) to about 4.5 N). With a hollow stylet having an outer diameter of about 0.5 mm (about 0.02 in) and a lumen or inner diameter of about 0.25 mm (about 0.01 in), a stylet holding force of about 0.1 lbf to about 0.5 lbf (about 0.4 N to about 2.2 N) may be generated. Such a force is sufficient to frictionally secure the stylet during typical extraction and catheter insertion activities.

Apparatus and systems in accordance with embodiments of the present invention may thus provide catheter retainers operable to immobilize a catheter, once implanted or otherwise positioned, from subsequent movement resulting from extraction of a catheter stylet. Moreover, stylet holders may be provided that provide a consistent and repeatable stylet clamping force selected to ensure adequate stylet retention without damage thereto. This clamping force may be generated by an internal biasing member, thereby minimizing clinician variability that may otherwise exist with conventional set screw holding techniques.

Illustrative embodiments of this invention are discussed and reference has been made to possible variations within the scope of this invention. These and other variations, combinations, and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. A system for immobilizing a catheter during extraction of a stylet located within a lumen of the catheter while at least a portion of the catheter is implanted in tissue, the system comprising:
    a cannula defining a cannula lumen configured to slidably receive therein the catheter and the stylet, the cannula comprising a first end; and
    a retainer configured to engage the first end of the cannula such that the retainer is restrained from longitudinal movement relative to the cannula, the retainer defining one or more surfaces configured to restrain longitudinal movement of the catheter relative to the retainer, the one or more surfaces further defining an opening sized to allow passage of the stylet through the retainer.

2. The system of claim 1, wherein the first end of the cannula comprises a flange.

3. The system of claim 1, wherein the one or more surfaces of the retainer is configured to contact a terminal end face of the catheter as the stylet is extracted.

4. The system of claim 3, wherein the opening is configured as an open-ended slot defined by a slot width that is smaller than an outer diameter of the catheter.

5. The system of claim 1, wherein the one or more surfaces is configured to contact a friction member positioned about the catheter, the friction member located between the cannula and the one or more surfaces.

6. The system of claim 1, wherein the retainer comprises a body defining a semi-cylindrically shaped recess configured to receive a cylindrically shaped head formed at the first end of the cannula.

7. A catheter delivery system comprising:
a tubular catheter having a distal end configured for implantation at a target site;
a guide cannula for directing the catheter to the target site, the guide cannula comprising: a proximal end comprising a flange; and a distal end positionable near the target site, wherein the guide cannula defines a cannula lumen for receiving the catheter, the cannula lumen extending from the proximal end to the distal end of the guide cannula;
a stylet configured for insertion into a proximal end of the catheter, the stylet adapted to engage an internal portion of the catheter and selectively push the catheter through the cannula lumen; and
a retainer operable to selectively engage the flange such that little or no relative longitudinal movement occurs between the retainer and the guide cannula, wherein the retainer comprises one or more surfaces configured to restrain the catheter from longitudinal movement, relative to the retainer, away from the target site.

8. The system of claim 7, further comprising a surgical apparatus configured to receive and immobilize the guide cannula.

9. The system of claim 8, wherein the surgical apparatus comprises a stereotactic frame.

10. The system of claim 7, wherein the one or more surfaces is configured to directly contact a terminal end face of the proximal end of the catheter as the stylet is extracted.

11. The system of claim 7, wherein the one or more surfaces is configured to contact a friction member interposed between the retainer and the catheter.

12. The system of claim 7, wherein the retainer may be engaged with the flange from a direction transverse to a longitudinal axis of the guide cannula.

* * * * *